United States Patent [19]

Torii et al.

[11] Patent Number: 4,629,542
[45] Date of Patent: Dec. 16, 1986

[54] PROCESS FOR PREPARING 3-EXOMETHYLENECEPHAM DERIVATIVES

[75] Inventors: Sigeru Torii; Hideo Tanaka, both of Okayama; Michio Sasaoka, Tokushima; Yutaka Kameyama, Okayama, all of Japan

[73] Assignee: Otsuka Kagaku Kabushiki Kaisha, Osaka, Japan

[21] Appl. No.: 707,767

[22] Filed: Mar. 4, 1985

[30] Foreign Application Priority Data

Mar. 6, 1984 [JP] Japan ................................. 59-43535

[51] Int. Cl.$^4$ ................................. C25B 3/00
[52] U.S. Cl. ................................. 204/72; 204/59 R; 204/73 R; 540/215; 540/222
[58] Field of Search ................. 204/59 R, 72, 73 R

[56] References Cited

U.S. PATENT DOCUMENTS 4,042,472  8/1977  Hall ................................. 204/59 R

OTHER PUBLICATIONS

J. Am. Chem. Soc., 98, 5040 (1976).

Primary Examiner—Arthur P. Demers
Attorney, Agent, or Firm—Armstrong, Nikaido, Marmelstein & Kubovcik

[57] ABSTRACT

This invention provides a process for preparing 3-exomethylenecepham derivatives represented by the formula

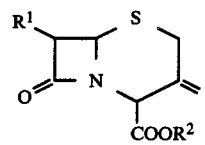

wherein $R^1$ is arylacetylamino, aryloxyacetylamino, heterocyclic acetylamino or imido, and $R^2$ is a protective group for the carboxyl, the process being characterized in that a 3-halomethylcephem compound represented by the formula

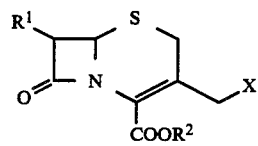

wherein $R^1$ and $R^2$ are as defined above, and X is a halogen atom is electrolyzed in a mixture of a hydrophilic organic solvent and water.

14 Claims, No Drawings

PROCESS FOR PREPARING 3-EXOMETHYLENECEPHAM DERIVATIVES

The present invention relates to a process for preparing 3-exomethylenecepham derivatives, and more particularly to a process for preparing 3-exomethylenecepham derivatives represented by the formula

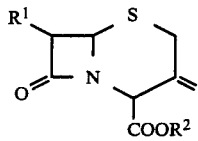

wherein $R^1$ is arylacetylamino, aryloxyacetylamino, heterocyclic acetylamino or imido, and $R^2$ is a protective group for the carboxyl.

The 3-exomethylenecepham derivative represented by the formula (I) is an important known compound as an intermediate for synthesizing cephalosporin antibiotics (see "Recent Advances in the Chemistry of β-Lactam Antibiotics", The Royal Society of Chemistry, Burinton House, London, p 15).

It is known to prepare 3-exomethylenecepham derivatives of the formula (I) by the chemical conversion of natural cephalosporin C or by deriving the compound from penicillin. The former process has the drawback that natural cephalosporin which is used as the starting material is expensive and is not readily available, so that the latter process which is advantageous in that the starting material is inexpensively available is widely used. The process represented by the following reaction scheme, for example, is known as a typical process for preparing 3-exomethylenecepham derivatives of the formula (I) from penicillin. According to this process, S-oxide (II) of penicillin is subjected to ring-opening chlorination in the presence of N-chlorosuccinimide, and the resulting azetidinone derivative (III) is subjected to a ring-closing reaction in the presence of stannic chloride to obtain 3-exomethylenecepham S-oxide derivative (IV), which is reduced to the desired 3-exomethylenecepham derivative (I) in the presence of a trivalent phosphorus compound (S. Kukolja et al., J. Am. Chem. Soc., 98, 5040 (1976)).

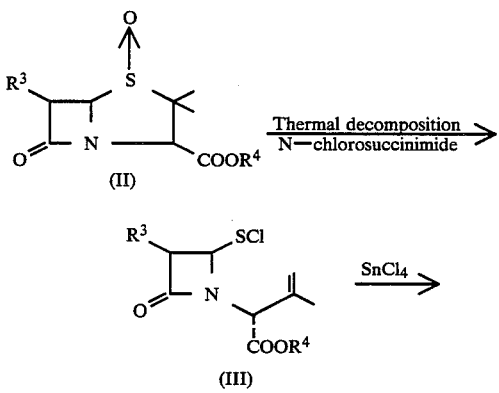

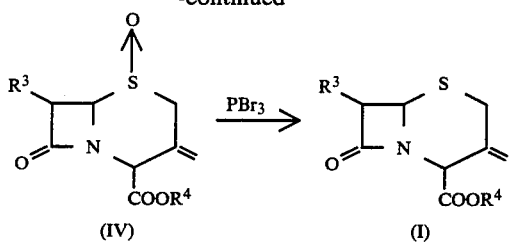

wherein $R^3$ is phthalimido or phenoxyacetylamino and $R^4$ is methyl or p-nitrobenzyl.

However, the above process requires at least equivalent moles of N-chlorosuccinimide for the ring-opening chlorination of penicillin S-oxide (II), at least equivalent moles of stannic chloride for the ring-closing reaction of the resulting azetidinone derivative (III), and further a large quantity of trivalent phosphorus compound for the reduction of the 3-exomethylenecepham S-oxide derivative (IV) obtained. The reagents used for the reactions of the process require special care for handling, while the reaction residues are harmful and are not disposable without an additional treatment. The process is therefore unsatisfactory for commercial operation.

Accordingly, an object of the present invention is to provide an industrially advantageous process for preparing 3-exomethylenecepham derivatives.

Another object of the invention is to provide a process for preparing 3-exomethylenecepham derivatives from an easily available material in high yields, with a high purity and by a simple reaction procedure.

Another object of the invention is to provide a process for preparing 3-exomethylenecepham derivatives without using reactants or catalysts which are harmful or difficult to handle.

Still another object of the invention is to provide a process for preparing 3-exomethylenecepham derivatives without entailing the problem of treatment for the disposal reaction residues.

The present invention provides a process for preparing a 3-exomethylenecepham derivative (I) by electrolyzing in a mixture of a hydrophilic organic solvent and water a 3-halomethylcephem compound represented by the formula

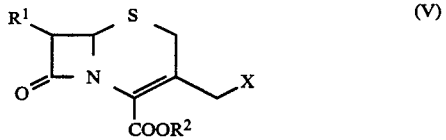

wherein $R^1$ and $R^2$ are as defined above, and X is a halogen atom.

In the course of research, we made an attempt to electrolyze a 3-halomethylcephem compound in the form of an aqueous solution of a water-soluble acid or salt of the compound. According to this process, however, a 3-exomethylenecepham derivative is obtained only in a very low yield with a by-product, 3-methylcephem derivative. In the subsequent research, we electrolyzed a 3-halomethylcephem compound in the form of a water-insoluble ester represented by the formula (V) in a mixture of a hydrophilic organic solvent and water to find the surprising result that the electrolytic process gives a 3-exomethylenecepham derivative (I) with good stability and high purity in a high yield.

By the process of the invention, the desired 3-exomethylenecepham derivative (I) can be prepared from a 3-halomethylcephem compound (V) which is readily available, with a high purity, in a high yield, by a simple reaction procedure and also through a simple isolation procedure. Furthermore, the process of the invention does not require reactants or catalysts which are difficult to handle or harmful and can therefore be practiced by a simple reaction procedure without entailing the problem of treating the reaction residue for disposal.

The 3-halomethylcephem compounds represented by the formula (V) and useful as the starting materials of the invention are all known compounds and can be prepared from penicillin with ease (Shigeru Torii et al., Tetrahydron Letter, 23, 2187 (1982)). The groups represented by $R^1$ in the formula (V) include arylacetylamino, aryloxyacetylamino, heterocyclic acetylamino and imido. These groups are known as 7-position substituents for cephalosporin or as 6-position substituents for penicillin and the groups represented by $R^1$ in the formula (V) include all of those substituents. More specifically, useful arylacetylamino groups include those optionally substituted on the aryl ring and those optionally substituted in the α-position of the acetyl moiety. Examples of substituents on the aryl ring are hydroxy, lower alkoxy, halogen and the like. Examples of substituents in the acetyl moiety are amino, sulfonyl, hydroxy, formyloxy, carbamoyl and the like. Preferred examples of arylacetylamino groups are phenylacetylamino groups optionally having such substituents. Specific examples thereof are phenylacetylamino, phenylglycylamino, p-hydroxyphenylglycylamino or N-acylated group thereof, α-sulfonylphenylacetylamino, α-hydroxyphenylacetylamino, α-formyloxyphenylacetylamino, α-carbamoylphenylacetylamino, p-methoxyphenylacetylamino, p-chlorophenylacetylamino, p-hydroxyphenylacetylamino, α-naphthylacetylamino, β-naphthylacetylamino, et.c. Of these preferable are phenylacetylamino, phenylglycylamino, p-hydroxyphenylglycylamino, α-sulfonylphenylacetylamino, α-hydroxyphenylacetylamino, α-formyloxyphenylacetylamino, p-hydroxyphenylacetylamino, etc. Useful aryloxyacetylamino groups include those optionally substituted on the aryl ring. Examples of substituents on the aryl ring are halogen, lower alkoxy and the like. Preferred examples of aryloxyacetylamino groups are phenoxyacetylamino groups optionally having such substituents. Specific examples thereof are phenoxyacetylamino, p-chlorophenoxyacetylamino, p-bromo phenoxyacetylamino, p-methoxyphenoxyacetylamino, etc. Of these preferable are phenoxyacetylamino, p-methoxyphenoxyacetylamino, etc. Useful heterocyclic acetylamino groups include those optionally substituted on the heterocyclic ring and those optionally substituted in the α-position of the acetyl moiety. Examples of substituents on the heterocyclic ring are amino, substituted amino, alkyl, substituted alkyl and the like. Examples of substituents in the acetyl moiety are amino, substituted amino, imino, substituted imino and the like. Preferred examples of heterocyclic rings are tetrazole, thienyl, thiazole, furyl, etc. Specific examples thereof are tetrazolylacetylamino, thienylacetylamino, 2-aminothiazolylacetylamino, furylacetylamino, α-hydroxyimino-2-aminothiazolylacetylamino, α-methoxyimino-2-aminothiazolylacetylamino, α-(1-carboxy-1-methylethoxy)imino-2-aminothiazolylacetylamino, α-methoxyiminofurylacetylamino, etc. Of these examples, preferable are tetrazolylacetylamino, α-hydroxyimino-2-aminothiazolylacetylamino, α-methoxyimino-2-aminothiazolylacetylamino, α-(1-carboxy-1-methylethoxy)imino-2-aminothiazolylacetylamino, α-methoxyiminofurylacetylamino, etc. Examples of useful imido groups are succinimido, phthalimido and imido having two acyl groups substituted on amino group, such as di(phenylacetyl)amino, di(phenoxyacetyl)amino, etc. Of these groups, preferable are succinimido, phthalimido, di(phenylacetyl)amino, di(phenoxyacetyl)amino, etc.

The protective groups disclosed by Theodora W. Greene in "Protective Groups in Organic Synthesis", Chapter 5 are usable as carboxy-protective groups represented by $R^2$ in the formula (V). Examples of useful protective groups are methyl, ethyl, propyl, tert-butyl and like lower alkyl group; methoxymethyl, methoxyethoxymethyl, i-propoxymethyl and like lower alkoxyalkyl group; 1-methoxycarbonyl-2-oxopropyl and like group represented by the formula of

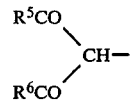

(wherein $R^5$ and $R^6$ are respectively lower alkyl and lower alkoxy): benzyl, o-nitrobenzyl, p-nitrobenzyl, o,p-dinitrobenzyl, p-methoxybenzyl, trimethoxybenzyl, trimethoxydichlorobenzyl, piperonyl and like benzyl group optionally having a substituent on the phenyl group; diphenylmethyl, bis(p-methoxyphenyl)methyl, ditolylmethyl, phenyl-p-methoxyphenylmethyl, trityl, α-diphenylethyl, α-p-methoxyphenylethyl and like mono-, di- or triphenylalkyl group optionally having a substituent on the phenyl group; phenacyl, p-bromophenacyl and like phenacyl group optionally having a substituent on the phenyl group; benzyloxymethyl; cumyl; fluorenyl; etc. Among these groups, especially preferable are tert-butyl, methoxymethyl, methoxyethoxymethyl, 1-methoxycarbonyl-2-oxopropyl benzyl, p-nitrobenzyl, p-methoxybenzyl, diphenylmethyl, phenacyl, benzyloxymethyl, etc. Examples of halogen atoms represented by X in the formula (V) are chlorine, bromine, iodine and like.

According to the present invention, it is essential that the 3-halomethylcephem compound of the formula (V) be electrolyzed in a mixture of a hydrophilic organic solvent and water. The hydrophilic organic solvents to be used are those which dissolve the starting material, i.e. 3-halomethylcephem compound (V) and which are stable under the reaction conditions. Examples of useful organic solvents are ethers such as tetrahydrofuran, dioxane and diethyl ether, nitriles such as acetonitrile and butyronitrile, alcohols such as methanol, ethanol, propanol, isopropanol, tert-butyl alcohol and ethylene glycol, ketones such as acetone, methyl ethyl ketone and diethyl ketone, dimethylformamide, dimethyl sulfoxide, etc. These hydrophilic organic solvents can be used singly, or at least two of them are usable in admixture. Further these hydrophilic organic solvents are usable as admixed with hydrophobic organic solvents insofar as the use of the latter does not impair the compatibility of the former with water.

The ratio of the hydrophilic organic solvent to water is not limited definitely but is variable with the kind of starting material, i.e. 3-halomethylcephem compound (V), etc. Usually, however, the former to latter ratio is about 100:1 to about 1:10, preferably about 20:1 to about 1:5, by weight. The amount of the mixture of hydrophilic organic solvent and water to be used is variable with the kind of 3-halomethylcephem compound used as the starting material and is not limited particularly. Usually, however, the mixture is used in about 0.3 to about 1000 times, preferably about 0.5 to about 500 times, the amount by weight of the compound (V).

In conducting the electrolytic reaction of the present invention, a support electrolyte is added to the reaction system. A wide variety of support electrolytes heretofore known in the art are usable. Examples of such electrolytes are alkali metal salts of perchloric acid such as $LiClO_4$ and $NaClO_4$, alkaline earth metal salts of perchloric acid such as $Mg(ClO_4)_2$, ammonium salts of perchloric acid such as $NH_4ClO_4$, $(CH_3)_4NClO_4$, $(C_2H_5)_4NClO_4$, alkali metal salts of borofluoric acid such as $LiBF_4$ and $NaBF_4$, alkali metal salts of hydrohalogenic acids such as NaCl, ammonium salts of hydrohalogenic acids such as $NH_4Cl$ and $NH_4Br$, ammonium salts of sulfuric acid such as $NH_4HSO_4$ and $(NH_4)_2SO_4$, alkali metal salts of sulfonic acids such as sodium p-toluenesulfonate and lithium p-toluenesulfonate, etc. Among these support electrolytes preferable are $LiClO_4$, $NaClO_4$, $Mg(ClO_4)_2$, $NH_4ClO_4$, $(CH_3)_4NClO_4$, $(C_2H_5)_4NClO_4$, etc. According to the invention, these support electrolytes are usable singly, or at least two of them can be used in admixture. The amount of such electrolyte to be used is not limited definitely but is variable with the kind of solvent used, etc. Usually the amount is about 0.1 to about 10% by weight, preferably about 0.1 to about 5% by weight, based on the solvent.

The electrolytic reduction of the present invention can be carried out in an unseparated single cell or in a separation cell wherein the anode and cathode chambers are separated by a partition. Electrodes which are widely used for usual electrolytic reactions are usable for the present invention. More specifically, examples of useful materials for the anode are platinum, stainless steel, carbon, iron oxide, surface-treated titanium, etc. Examples of suitable materials for the cathode are zinc, lead, copper, nickel, stainless steel, platinum, carbon, etc.

The electrolysis of the present invention can be conducted at a constant potential or constant current value. However, from the viewpoint of the apparatus and ease of operation, it is desirable to use the constant-current electrolytic process. The current density is usually about 1 to about 500 $mA/cm^2$, preferably about 5 to about 50 $mA/cm^2$. The electrolysis carried out usually at a temperature of about -10° to about 50° C., preferably about 0° to about 30° C. The amount of electricity to be passed is not limited definitely but is variable with the type of cell to be used, the kind of starting material, i.e. 3-halomethylcephem compound (V), the kind of solvent to be used, etc. Usually the amount is about 2 to about 10 F., preferably about 2 to about 7 F., per mole of the starting material. When the above amount of electricity has been passed, the reaction is completed.

After the completion of the electrolytic reaction, the electrolytic solution is concentrated and then subjected to a usual extraction process, whereby the desired 3-exomethylenecepham derivative (I) can be obtained as a substantially pure product. When required, the product may be purified by a conventional method such as recrystallization, column chromatography or the like.

For a better understanding of the present invention, examples are given below. "Ph" stands for phenyl.

EXAMPLE 1

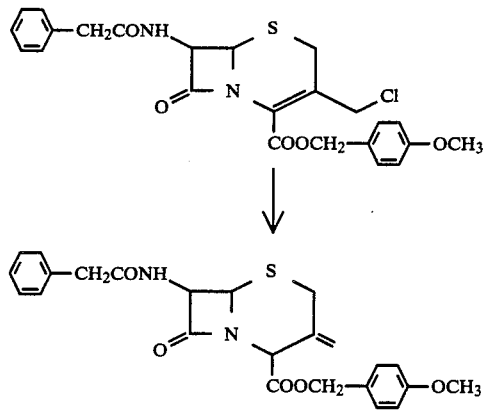

An H-shaped tubular separation cell was prepared in which the anode and cathode chambers were separated by a glass filter. Into the anode and cathode chambers were placed a solution prepared from 12 ml of tetrahydrofuran, 3 ml of water, 330 mg of $LiClO_4$ and 467 mg of $NH_4ClO_4$. A 51 mg quantity of p methoxybenzyl 7-phenylacetamido-3-chloromethylcephem-4-carboxylate was placed into the cathode chamber and made into a uniform solution with stirring. Next, a platinum anode (1.5 $cm^2$ in surface area) and a lead cathode (1.5 $cm^2$ in surface area) were set in place. The solution was then subjected to electrolysis at a constant current density of 6.6 $mA/cm^2$ at room temperature for 85 minutes by passing 5 F/mol of electricity. The electrolytic solution was then drawn off from the cathode chamber and distilled in a vacuum to remove the solvents. The residue was subjected to extraction with ethyl acetate, and the extract was washed with saturated aqueous solution of sodium chloride twice and dried over anhydrous sodium sulfate. The extract was thereafter concentrated in a vacuum, giving white crystals.

The crude crystals obtained were subjected to silica gel column chromatography, affording 41.1 mg (yield: 87%) of p-methoxybenzyl 7-phenylacetamide-3-exomethylenecepham-4-carboxylate as a pure product.

Table 5 shows the result of NMR analysis of the product obtained.

EXAMPLES 2-8

The same procedure as in Example 1 was repeated except that the electrodes were replaced by those listed in Table 1. The results of NMR analysis of the products were in agreement with the result achieved by the product of Example 1.

TABLE 1

| Example | Anode | Cathode | Yield (%) |
|---------|----------|---------|-----------|
| 2 | Carbon | Lead | 90 |
| 3 | Carbon | Copper | 85 |
| 4 | Platinum | Copper | 93 |
| 5 | Platinum | Nickel | 85 |
| 6 | Carbon | Carbon | 85 |
| 7 | Platinum | Carbon | 88 |

TABLE 1-continued

| Example | Anode | Cathode | Yield (%) |
|---|---|---|---|
| 8 | Platinum | Zinc | 86 |

EXAMPLES 9–16

The same procedure as in Example 2 was repeated except that some conditions were changed to those listed in Table 2. The results of NMR analysis of the products were in agreement with the result achieved by the product of Example 1. THF stands of tetrahydrofuran.

TABLE 2

| Example | Solvent (ml) | Quantity of electricity (F/mol) | Yield (%) |
|---|---|---|---|
| 9 | $CH_3CN$ (12), $H_2O$ (3), $C_2H_5OH$ (0.5) | 7.0 | 95 |
| 10 | THF (12), $H_2O$ (3), $C_2H_5CH$ (0.5) | 5.0 | 85 |
| 11 | Dioxane (12), $H_2O$ (3) | 6.0 | 86 |
| 12 | $CH_3COOC_2H_5$ (7), THF (5), $H_2O$ (3) | 8.0 | 92 |
| 13 | $CH_3CN$ (10), $H_2O$ (3), THF (2), $t$-$C_4H_9OH$ (0.5) | 5.0 | 87 |
| 14 | THF (11), $H_2O$ (3), Acetone (1), $C_2H_5OH$ (0.5) | 5.0 | 88 |
| 15 | THF (10), $H_2O$ (20) | 5.0 | 86 |
| 16 | THF (10), $H_2O$ (10) | 5.0 | 88 |

EXAMPLES 17–19

The same procedure as in Example 1 was repeated except that some conditions were changed to those listed in Table 3. The results of NMR analysis of the products were in agreement with the result achieved by the product of Example 1.

TABLE 3

| Example | Support salt (mg) | Quantity of electricity (F/mol) | Yield (%) |
|---|---|---|---|
| 17 | $NaClO_4$ (300), $(C_2H_5)_4NClO_4$ (550) | 7.0 | 85 |
| 18 | $LiClO_4$ (300), $(CH_3)_4NClO_4$ (520) | 6.0 | 86 |
| 19 | $Mg(ClO_4)_2$ (330), $NH_4ClO_4$ (530) | 7.5 | 90 |

EXAMPLES 20–29

The same procedure as in Example 1 was repeated with the exception of using the compound and the quantity of electricity listed in Table 4 to obtain the desired product. Table 5 shows the results achieved.

TABLE 4

| | Formula (V) | | | Quantity of electricity | Yield |
|---|---|---|---|---|---|
| Example | $R^1$ | $R^2$ | X | (F/mol) | (%) |
| 20 | $PhCH_2CONH-$ | $p$-$CH_3O-PH-CH_2-$ | I | 5.5 | 94 |
| 21 | $PhCH_2CONH-$ | $p$-$CH_3O-Ph-CH_2-$ | Br | 5.7 | 85 |
| 22 | $PhOCH_2CONH-$ | $p$-$CH_3O-Ph-CH_2-$ | Cl | 6.0 | 88 |
| 23 | $PhOCH_2CONH-$ | $p$-$NO_2-Ph-CH_2-$ | Cl | 5.8 | 91 |
| 24 | $PhOCH_2CONH-$ | $p$-$NO_2-Ph-CH_2-$ | I | 5.0 | 85 |
| 25 | (2-thienyl)-$CH_2CONH-$ | $p$-$CH_3O-PhCH_2-$ | Cl | 5.0 | 89 |
| 26 | (2-thienyl)-$CH_2CONH-$ | $p$-$NO_2-PhCH_2$ | Br | 5.0 | 90 |
| 27 | phthalimido- | $p$-$CH_3O-PhCH_2-$ | Cl | 5.0 | 93 |
| 28 | phthalimido- | $CH_3-$ | Br | 5.0 | 92 |
| 30 | $PhCH_2CONH-$ | $PhCH_2-$ | Cl | 5.0 | 91 |

EXAMPLE 30

In the same manner as in Example 1 except that 510 mg quantity of p-methoxybenzyl 7-phenylacetamide-3-chloromethylcephem-4-carboxylate was used to obtain p-methoxybenzyl 7-phenylacetamide-3-exthomethylenecepham-4-carboxylate in a yield of 87%. The result of NMR analysis thereof was in agreement with the result of the product of Example 1.

TABLE 5

| Formula (I) R¹ | R² | NMR (δ, ppm) |
|---|---|---|
| PhCH₂CONH— | p-CH₃O—PhCH₂— | 3.20 (ABq, 2H), 3.46 (s, 2H), 3.67 (s, 3H), 4.95 (s, 1H), 4.97 (s, 2H), 5.05 (bs, 2H), 5.20 (d, 1H), 5.50 (dd, 1H), 6.40 (d, 1H), 6.78 (d, 2H), 7.13 (d, 2H), 7.17 (bs, 5H) |
| PhOCH₂CONH— | p-CH₃O—PhCH₂— | 3.35 (ABq, 2H), 3.79 (s, 3H), 4.51 (s, 2H), 5.08–5.52 (m, 6H), 5.65 (q, 1H), 6.85–7.45 (m, 10H) |
| PhOCH₂CONH— | p-NO₂—PhCH₂— | 3.42 (ABq, 2H), 4.54 (s, 2H), 5.20–5.50 (m, 6H), 5.74 (q, 1H), 6.80–8.35 (m, 10H) |
| 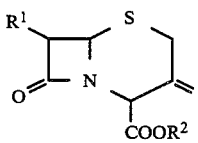 | p-CH₃O—PhCH₂— | 3.35 (ABq, 2H), 3.81 (s, 5H), 5.05–5.25 (m, 5H), 5.35 (d, 1H), 5.62 (q, 1H), 6.70–7.42 (m, 8H) |
| 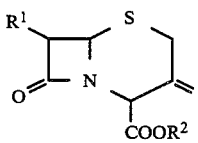 | p-NO₂—PhCH₂— | 3.57 (ABq, 2H), 3.83 (s, 2H), 5.30–5.70 (m, 7H), 6.90–8.84 (m, 8H) |
| 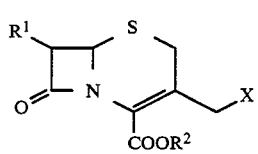 | p-NO₂—PhCH₂— | 3.51 (ABq, 2H), 5.37 (s, 5H), 5.43 (d, 1H), 5.61 (d, 1H), 7.40–8.30 (m, 8H) |
| 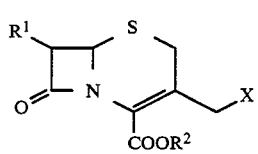 | CH₃— | 3.46 (ABq, 2H), 3.80 (s, 3H), 5.31 (m, 3H), 5.46 (d, 1H), 5.67 (d, 1H), 7.84 (m, 8H) |
| PhCH₂CONH— | PhCH₂— | 3.20 (ABq, 2H), 3.57 (s, 2H), 5.2–5.40 (m, 6H), 5.62 (dd, 1H), 6.35 (d, 1H), 7.15–7.50 (m, 10H) |

We claim:

1. A process for preparing 3-exomethylenecepham derivatives represented by the formula $$\begin{array}{c} R^1 \\ \diagdown \\ O= \end{array} \begin{array}{c} S \\ \diagup \\ N \end{array} \begin{array}{c} \\ \diagdown \\ COOR^2 \end{array}$$

wherein $R_1$ is arylacetylamino, aryloxyacetylamino, heterocyclic acetylamino or imido, and $R_2$ is a protective group for the carboxyl which protective group combined with the carboxyl group forms an ester, the process comprising selecting a 3-halomethylcephem compound represented by the formula $$\begin{array}{c} R^1 \\ \diagdown \\ O= \end{array} \begin{array}{c} S \\ \diagup \\ N \end{array} \begin{array}{c} \\ \diagdown \\ COOR^2 \end{array} X$$

wherein $R^1$ and $R^2$ are as defined above, and X is a halogen atom, and electrolyzing the selected compound in a mixture of a hydrophilic organic solvent and water.

2. A process as defined in claim 1 wherein the hydrophilic organic solvent is a solvent which dissolves the starting material and is stable under the reaction conditions.

3. A process as defined in claim 1 wherein the hydrophilic organic solvent to water ratio of the mixture is about 100:1 to about 1:10 by weight.

4. A process as defined in claim 3 wherein the hydrophilic organic solvent to water ratio of the mixture is about 20:1 to about 1:5 by weight.

5. A process as defined in claim 1 wherein the mixture of hydrophilic organic solvent and water is used in about 0.3 to about 1000 times the amount by weight of the starting material.

6. A process as defined in claim 1 wherein the electrolysis is conducted in the presence of a support electrolyte.

7. A process as defined in claim 1 wherein the electrolysis is conducted at a current density of about 1 to about 500 mA/cm².

8. A process as defined in claim 7 wherein the electrolysis is conducted at a current density of about 5 to about 50 mA/cm².

9. A process as defined in claim 1 wherein the electrolysis is conducted at a temperature of about −10° to about 50° C.

10. A process as defined in claim 9 wherein the electrolysis is conducted at a temperature of about 0° to about 30° C.

11. A process as defined in claim 1 wherein the electrolysis is conducted at an amount of electricity of about 2 to about 10 F. per mole of the starting material.

12. A process as defined in claim 1 wherein the protective group for the carboxyl is selected from the following: lower alkyl group, lower alkoxyalkyl group, the group represented by the formula

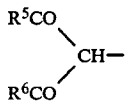

wherein $R^5$ and $R^6$ are lower alkyl and lower alkoxy, respectively, benzyl group, benzyl group having a substituent on the phenyl group, mono-, di- or triphenylalkyl group, mono-, di-, or triphenyl- alkyl group having a substituent on the phenyl group, phenacyl group, phenacyl group having a substituent on the phenyl group, benzyloymethyl, cumyl or fluorenyl.

13. A process as defined in claim 12 wherein the substitutent for the benzyl group is at least one of nitro, methoxy, chlorine atom and methylenedioxy, the substituent for the phenylalkyl group is at least one of methoxy and methyl, and the substituent for the phenacyl group is bromine atom.

14. A process as defined in claim 12 wherein the protective group for the carboxyl is tert-butyl, methoxy-methyl, methoxyethoxymethyl, 1-methoxycarbonyl-2-oxopropyl, benzyl, p-nitrobenzyl, p-methoxybenzyl, diphenylmethyl, phenacyl or benzyloxymethyl.

* * * * *